United States Patent
Browne et al.

(10) Patent No.: US 10,407,707 B2
(45) Date of Patent: Sep. 10, 2019

(54) CELL CULTURING DEVICE

(71) Applicant: Rapid Micro Biosystems, Inc., Lowell, MA (US)

(72) Inventors: Douglas J. Browne, Groton, MA (US); Sarkis Karakozian, Belmont, MA (US); Xiaowei Chen, Lexington, MA (US)

(73) Assignee: Rapid Micro Biosystems, Inc., Lowell, MA (US)

( * ) Notice: Subject to any disclaimer, the term of this patent is extended or adjusted under 35 U.S.C. 154(b) by 352 days.

(21) Appl. No.: 14/394,505

(22) PCT Filed: Apr. 16, 2013

(86) PCT No.: PCT/US2013/036816
§ 371 (c)(1),
(2) Date: Oct. 15, 2014

(87) PCT Pub. No.: WO2013/158666
PCT Pub. Date: Oct. 24, 2013

(65) Prior Publication Data
US 2015/0072377 A1    Mar. 12, 2015

Related U.S. Application Data

(60) Provisional application No. 61/624,643, filed on Apr. 16, 2012.

(51) Int. Cl.
*C12M 1/00*     (2006.01)
*C12M 1/22*     (2006.01)
*C12Q 1/04*     (2006.01)

(52) U.S. Cl.
CPC ............... *C12Q 1/04* (2013.01); *C12M 23/10* (2013.01); *C12M 23/38* (2013.01)

(58) Field of Classification Search
CPC .......... C12Q 1/04; C12M 23/10; C12M 23/38
See application file for complete search history.

(56) References Cited

U.S. PATENT DOCUMENTS

| | | |
|---|---|---|
| 2,672,431 A | 3/1954 | Goetz |
| 2,761,813 A | 9/1956 | Goetz |

(Continued)

FOREIGN PATENT DOCUMENTS

| | | |
|---|---|---|
| AU | 760425 B2 | 5/2003 |
| CN | 85106361 A | 4/1986 |

(Continued)

OTHER PUBLICATIONS

Synbiosis, "What's New: Innovative Plate Holder for ProtoCOL," <http://www.synbiosis.com/synbiosis/moreinfo.asp?page=BR29>, retrieved Oct. 16, 2002 (2 pages).

(Continued)

*Primary Examiner* — William H. Beisner
*Assistant Examiner* — Danielle B Henkel
(74) *Attorney, Agent, or Firm* — Clark & Elbing LLP

(57) ABSTRACT

The invention features devices and kits for capturing and culturing microorganisms (e.g., bacteria, fungi, or protists) and methods of using the devices and kits to detect microorganisms in environmental and other samples. The device includes a nutrient media having a flat growth area on which microorganisms can grow. Samples are collected by contacting the device with any environmental sample, e.g., rolling device on a work surface or exposing device to air, or by filtering a sample through a membrane. Microorganisms deposited on the membrane derive nutrients from the underlying media and grow into colonies that can then be detected using methods known in the art. The detected colonies can be imaged digitally or with film.

39 Claims, 17 Drawing Sheets

A
With protective lid

1 Base
2 Nutrient media
3 ID label
4 Protective lid
5 Film
6 Membrane

B
With optical lid

(56) References Cited

U.S. PATENT DOCUMENTS

| | | |
|---|---|---|
| 3,694,317 A | 9/1972 | Scher |
| 3,981,776 A | 9/1976 | Saxholm |
| 4,097,586 A | 6/1978 | Gross |
| 4,098,876 A | 7/1978 | Piasio et al. |
| 4,115,535 A | 9/1978 | Giaever |
| 4,125,375 A | 11/1978 | Hunter |
| 4,129,419 A | 12/1978 | Hermann, Jr. |
| 4,141,687 A | 2/1979 | Forrest et al. |
| 4,157,323 A | 6/1979 | Yen et al. |
| 4,177,253 A | 12/1979 | Davies et al. |
| 4,222,744 A | 9/1980 | McConnell |
| 4,436,826 A | 3/1984 | Wang |
| 4,438,068 A | 3/1984 | Forrest |
| 4,454,233 A | 6/1984 | Wang |
| 4,455,370 A | 6/1984 | Bartelsman et al. |
| 4,477,578 A | 10/1984 | Miles et al. |
| 4,537,861 A | 8/1985 | Elings et al. |
| 4,562,157 A | 12/1985 | Lowe et al. |
| 4,565,783 A | 1/1986 | Hansen et al. |
| 4,582,810 A | 4/1986 | Rosenstein |
| 4,587,213 A | 5/1986 | Malecki |
| 4,598,050 A | 7/1986 | Brown |
| 4,614,585 A | 9/1986 | Mehra et al. |
| 4,693,972 A | 9/1987 | Mansour et al. |
| 4,731,337 A | 3/1988 | Luotola et al. |
| 4,745,077 A | 5/1988 | Holian et al. |
| 4,750,820 A | 6/1988 | Pareigat |
| 4,775,628 A | 10/1988 | Takakura et al. |
| 4,777,137 A | 10/1988 | Lemonnier |
| 4,777,145 A | 10/1988 | Luotola et al. |
| 4,912,037 A | 3/1990 | Lemonnier |
| 4,922,092 A | 5/1990 | Rushbrooke et al. |
| 4,959,301 A | 9/1990 | Weaver et al. |
| 4,981,783 A | 1/1991 | Augenlicht |
| 4,988,302 A | 1/1991 | Smith et al. |
| 4,988,618 A | 1/1991 | Li et al. |
| 5,073,497 A | 12/1991 | Schwartz |
| 5,089,413 A | 2/1992 | Nelson et al. |
| 5,130,733 A | 7/1992 | Taniguchi et al. |
| 5,137,812 A | 8/1992 | Matner |
| 5,190,666 A | 3/1993 | Bisconte |
| 5,232,838 A | 8/1993 | Nelson et al. |
| 5,238,810 A | 8/1993 | Fujiwara et al. |
| 5,258,284 A | 11/1993 | Morris, Jr. et al. |
| 5,262,526 A | 11/1993 | Sasamoto et al. |
| 5,292,644 A | 3/1994 | Berg |
| 5,306,420 A | 4/1994 | Bisconte |
| 5,321,545 A | 6/1994 | Bisconte |
| 5,348,885 A | 9/1994 | Labarthe |
| 5,355,215 A | 10/1994 | Schroeder et al. |
| 5,366,867 A | 11/1994 | Kawakami et al. |
| 5,464,749 A | 11/1995 | Schwarzberg et al. |
| 5,474,910 A | 12/1995 | Alfano |
| 5,510,246 A | 4/1996 | Morgan |
| 5,538,857 A | 7/1996 | Rosenthal et al. |
| 5,541,069 A | 7/1996 | Mortensen et al. |
| 5,552,272 A | 9/1996 | Bogart |
| 5,558,839 A | 9/1996 | Matte et al. |
| 5,582,982 A | 12/1996 | Cubbage et al. |
| 5,585,241 A | 12/1996 | Lindmo |
| 5,604,351 A | 2/1997 | Bisconte |
| 5,606,413 A | 2/1997 | Bellus et al. |
| 5,624,850 A | 4/1997 | Kumar et al. |
| 5,653,939 A | 8/1997 | Hollis et al. |
| 5,663,057 A | 9/1997 | Drocourt et al. |
| 5,672,880 A | 9/1997 | Kain |
| 5,681,530 A | 10/1997 | Kuster et al. |
| 5,681,712 A | 10/1997 | Nelson |
| 5,694,478 A | 12/1997 | Braier et al. |
| 5,705,402 A | 1/1998 | Leland et al. |
| 5,736,405 A | 4/1998 | Alfano et al. |
| 5,744,322 A | 4/1998 | Krejcarek et al. |
| 5,766,868 A | 6/1998 | Seto |
| 5,792,617 A | 8/1998 | Rotman |
| 5,814,454 A | 9/1998 | Ju |
| 5,821,066 A | 10/1998 | Pyle et al. |
| 5,828,716 A | 10/1998 | Bisconte de Saint Julien |
| 5,843,766 A | 12/1998 | Applegate et al. |
| 5,852,498 A | 12/1998 | Youvan et al. |
| 5,861,251 A | 1/1999 | Park et al. |
| 5,861,270 A | 1/1999 | Nelis |
| 5,861,306 A | 1/1999 | Pugh et al. |
| 5,891,394 A | 4/1999 | Drocourt et al. |
| 5,914,245 A | 6/1999 | Bylina et al. |
| 5,958,790 A | 9/1999 | Cerny |
| 5,968,766 A | 10/1999 | Powers |
| 5,976,892 A | 11/1999 | Bisconte |
| 5,981,180 A | 11/1999 | Chandler et al. |
| 5,985,675 A | 11/1999 | Charm et al. |
| 5,993,740 A | 11/1999 | Niiyama et al. |
| 6,048,723 A | 4/2000 | Banes |
| 6,051,395 A | 4/2000 | Rocco |
| 6,121,055 A | 9/2000 | Hargreaves |
| 6,122,396 A | 9/2000 | King et al. |
| 6,130,931 A | 10/2000 | Laurila et al. |
| 6,140,653 A | 10/2000 | Che |
| 6,165,742 A | 12/2000 | Ofjord et al. |
| 6,171,780 B1 | 1/2001 | Pham et al. |
| 6,200,762 B1 | 3/2001 | Zlokarnik et al. |
| 6,214,560 B1 | 4/2001 | Yguerabide et al. |
| 6,258,326 B1 | 7/2001 | Modlin |
| 6,259,807 B1 | 7/2001 | Ravkin |
| 6,268,222 B1 | 7/2001 | Chandler et al. |
| 6,274,384 B1 | 8/2001 | Starzl et al. |
| 6,287,849 B1 | 9/2001 | McNerney et al. |
| 6,306,589 B1 | 10/2001 | Muller et al. |
| 6,309,822 B1 | 10/2001 | Fodor et al. |
| 6,345,115 B1 | 2/2002 | Ramm et al. |
| 6,358,730 B1 | 3/2002 | Kane |
| 6,472,166 B1 | 10/2002 | Wardlaw et al. |
| 6,582,912 B1 | 6/2003 | Rousseau et al. |
| 6,602,704 B1 | 8/2003 | Maxwell et al. |
| 6,623,983 B1 | 9/2003 | Terstappen et al. |
| 6,664,528 B1 | 12/2003 | Cartlidge et al. |
| 6,710,879 B1 | 3/2004 | Hansen et al. |
| 6,727,071 B1 | 4/2004 | Dunlay et al. |
| 6,764,648 B1 | 7/2004 | Roach et al. |
| 6,790,655 B2 | 9/2004 | Lyman et al. |
| 6,792,132 B1 | 9/2004 | Hara et al. |
| 6,852,527 B2 | 2/2005 | Chan et al. |
| 6,919,960 B2 | 7/2005 | Hansen et al. |
| 6,969,607 B2 | 11/2005 | Minton |
| 7,068,365 B2 | 6/2006 | Hansen et al. |
| 7,160,687 B1 | 1/2007 | Kapur et al. |
| 7,582,415 B2 | 9/2009 | Straus |
| 7,763,405 B2 | 7/2010 | Wu et al. |
| 7,763,455 B2 | 7/2010 | Cima et al. |
| 7,820,430 B2 | 10/2010 | Weng et al. |
| 9,057,046 B2 | 6/2015 | Browne et al. |
| 9,745,546 B2 | 8/2017 | Aviles et al. |
| 2001/0039060 A1 | 11/2001 | Siiman et al. |
| 2002/0028471 A1 | 3/2002 | Oberhardt |
| 2002/0055092 A1 | 5/2002 | Hochman |
| 2002/0137106 A1 | 9/2002 | Leung et al. |
| 2004/0048395 A1 | 3/2004 | Lee et al. |
| 2004/0171121 A1 | 9/2004 | Leppla et al. |
| 2004/0172000 A1 | 9/2004 | Roe et al. |
| 2004/0246483 A1 | 12/2004 | Hansen et al. |
| 2005/0013737 A1 | 1/2005 | Chow et al. |
| 2005/0148085 A1 | 7/2005 | Larsen |
| 2005/0153430 A1 | 7/2005 | Ohtaka |
| 2005/0191687 A1 | 9/2005 | Wang et al. |
| 2005/0220670 A1 | 10/2005 | Palmieri et al. |
| 2005/0221403 A1 | 10/2005 | Gazenko |
| 2005/0225766 A1 | 10/2005 | Hansen et al. |
| 2005/0226779 A1 | 10/2005 | Oldham et al. |
| 2006/0006067 A1 | 1/2006 | Unger |
| 2006/0051816 A1 | 3/2006 | Hsieh et al. |
| 2006/0121055 A1 | 6/2006 | Campbell et al. |
| 2006/0129327 A1 | 6/2006 | Kim et al. |
| 2006/0188967 A1 | 8/2006 | Nalin et al. |
| 2006/0210435 A1 | 9/2006 | Alavie et al. |
| 2006/0216696 A1 | 9/2006 | Goguen |
| 2006/0256340 A1 | 11/2006 | Hansen et al. |

(56) References Cited

U.S. PATENT DOCUMENTS

| | | |
|---|---|---|
| 2006/0292552 A1 | 12/2006 | Haquette et al. |
| 2007/0014695 A1 | 1/2007 | Yue et al. |
| 2007/0105185 A1 | 5/2007 | Cima et al. |
| 2007/0184546 A1 | 8/2007 | Farrelly et al. |
| 2007/0212681 A1 | 9/2007 | Shapiro et al. |
| 2007/0212747 A1 | 9/2007 | Browne et al. |
| 2008/0003571 A1 | 1/2008 | McKernan et al. |
| 2008/0014576 A1 | 1/2008 | Jovanovich et al. |
| 2008/0032328 A1 | 2/2008 | Cline et al. |
| 2008/0038738 A1 | 2/2008 | Weigum et al. |
| 2008/0200343 A1 | 8/2008 | Clemens et al. |
| 2008/0206099 A1 | 8/2008 | Aruga et al. |
| 2009/0311776 A1 | 12/2009 | Kelly, Jr. et al. |
| 2013/0011566 A1 | 1/2013 | Colin et al. |
| 2014/0342447 A1 | 11/2014 | Aviles et al. |
| 2016/0160166 A1 | 6/2016 | Niedl et al. |

FOREIGN PATENT DOCUMENTS

| | | |
|---|---|---|
| CN | 1249778 A | 4/2000 |
| CN | 2486557 Y | 4/2002 |
| CN | 101528912 A | 9/2009 |
| DE | 19608320 A1 | 8/1997 |
| DE | 19631997 A1 | 2/1998 |
| DE | 19940810 A1 | 5/2000 |
| EP | 0171174 A2 | 2/1986 |
| EP | 0574977 A1 | 12/1993 |
| EP | 1207394 A2 | 5/2002 |
| EP | 1508374 A2 | 2/2005 |
| EP | 1826263 A1 | 8/2007 |
| EP | 1985693 A1 | 10/2008 |
| EP | 2235203 B1 | 10/2014 |
| JP | H3-83598 A | 4/1991 |
| JP | H3-102240 A | 4/1991 |
| JP | H06-189739 A | 7/1994 |
| JP | 3017172 U | 10/1995 |
| JP | H10-295362 A | 11/1998 |
| JP | H11-346795 A | 12/1999 |
| JP | 2000509827 A | 8/2000 |
| JP | 2001-95557 A | 4/2001 |
| JP | 2001-512875 A | 8/2001 |
| JP | 2001224355 A | 8/2001 |
| JP | 2002506632 A | 3/2002 |
| JP | 2002125656 A | 5/2002 |
| JP | 2003294596 A | 10/2003 |
| JP | 2004-344087 A | 12/2004 |
| JP | 2006-505802 A | 2/2006 |
| JP | 2006087336 A | 4/2006 |
| JP | 2006-162466 A | 6/2006 |
| JP | 2008-96223 A | 4/2008 |
| JP | 2009513111 A | 4/2009 |
| JP | 2010-276387 A | 12/2010 |
| JP | 2012-024032 A | 2/2012 |
| WO | WO-83/01581 A1 | 5/1983 |
| WO | WO-86/04684 A1 | 8/1986 |
| WO | WO-89/05456 A1 | 6/1989 |
| WO | WO-92/05448 A2 | 4/1992 |
| WO | WO-93/24608 A1 | 12/1993 |
| WO | WO-97/40181 A1 | 10/1997 |
| WO | WO-97/44664 A1 | 11/1997 |
| WO | WO-98/31783 A1 | 7/1998 |
| WO | WO-98/38490 A1 | 9/1998 |
| WO | WO-98/50577 A1 | 11/1998 |
| WO | WO-99/08233 A1 | 2/1999 |
| WO | WO-99/20789 A1 | 4/1999 |
| WO | WO-99/36577 A1 | 7/1999 |
| WO | WO-99/40176 A1 | 8/1999 |
| WO | WO-99/47637 A1 | 9/1999 |
| WO | WO-99/58948 A2 | 11/1999 |
| WO | WO-00/04382 A1 | 1/2000 |
| WO | WO-00/47766 A1 | 8/2000 |
| WO | WO-01/57522 A2 | 8/2001 |
| WO | WO-01/61348 A1 | 8/2001 |
| WO | WO-2004/040260 A2 | 5/2004 |
| WO | WO-2005/082254 A2 | 9/2005 |
| WO | WO-2006/032044 A2 | 3/2006 |
| WO | WO-2008/005998 A2 | 1/2008 |
| WO | WO-2011/117545 A1 | 9/2011 |
| WO | WO-2013/070730 A2 | 5/2013 |

OTHER PUBLICATIONS

Perceptive Instruments Ltd., "Sorcerer Automated Colony Counting," <www.perceptive.co.uk>, (2 pages) (2002).

Perceptive Instruments Ltd., "Technical Specification," <http://www.perceptive.co.uk/products/scc/techspec.htm>, retrieved Apr. 12, 2005 (2 pages).

Al-Hakiem et al., "Development of fluoroimmunoassays for the determination of individual or combined levels of procainamide and n-acetylprocainamide in serum." J Immunoassay. 3(1):91-110 (1982).

Allman et al., "Fluoroimmunoassay of progesterone in human serum or plasma," Clin Chem. 27(7):1176-9 (1981).

BioLogics, "Colony Counter Models and Specifications," <http://biologics-inc.com/cc-models.htm>, retrieved Apr. 15, 2005 (3 pages).

Catalogue of Becton, Dickinson and Company, p. 28, 29, 32-35, 150 and 151, Japan, (2003).

Clean Technology, 5(8), 60-61 (1995) (No English translation provided).

Corkidi et al., "COVASIAM: an image analysis method that allows detection of confluent microbial colonies and colonies of various sizes for automated counting," Appl Environ Microbiol. 64(4)1400-4 (1998).

Loats Associates, Inc., "Digital Multi-Purpose High-Resolution Colony and Plaque Counter",<http://www.loats.com/mla.html>, retrieved Apr. 12, 2005 (3 pages).

Esteban et al., "Improved direct epifluorescent filter technique for rapid bioburden control in intravenous solutions." J Parenter Sci Technol. 46(5):146-9 (1992).

Findlay et al., "Automated closed-vessel system for in vitro diagnostics based on polymerase chain reaction," Clin Chem. 39(9):1927-33 (1993).

Freydiere et al., "Detection of salmonellae by using Rambach agar and by a C8 esterase spot test," J Clin Microbiol. 29(10):2357-9 (1991).

Frost, "Improved technic for the micro or little plate method of counting bacteria in milk," J Infect Dis. 28(2):176-184 (1921).

Gray et al., "Identification of micro-organisms after milliflex rapid detection—a possibility to identify nonsterile findings in the milliflex rapid sterility test," PDA J Pharm Sci Technol. 65(1):42-54 (2011).

International Search Report for International Patent Application No. PCT/US2013/036816, dated Aug. 13, 2013 (4 pages).

Kamentsky, "Laser scanning cytometry," Methods Cell Biol. 63: 51-87 (2001).

Kepner et al., "Use of fluorochromes for direct enumeration of total bacteria in environmental samples: past and present," Microbiol Rev. 58(4):603-15 (1994).

Kroll et al., "A laser-light pulse counting method for automatic and sensitive counting of bacteria stained with acridine orange," J Appl Bacteriol. 66(2):161-7 (1989).

Lamture et al., "Direct detection of nucleic acid hybridization on the surface of a charge coupled device," Nucleic Acids Res. 22(11): 2121-5 (1994).

Loats Associates Inc. System Specifications, "Ordering from Loats Associates, Inc.," <http://www.loats.com/order_info.html>, retrieved Apr. 12, 2005 (7 pages).

Loats et al., "LAI high-resolution automated colony counting system—mouse lymphoma assay: performance analysis,"<http://loats.com/docs/HRCCval/HRCCval.htm>, retrieved on Jul. 6, 2004 (11 pages).

Logtenberg et al., "Enumeration of (auto)antibody producing cells in human using the "spot-ELISA"," Immunol Lett. 9(6): 343-347 (1985).

London et al., "An automated system for rapid non-destructive enumeration of growing microbes," PLoS One. 5(1):e8609 (16 pages) (2010).

(56) References Cited

OTHER PUBLICATIONS

Masuko et al., "A novel method for detection and counting of single bacteria in a wide field using an ultra-high-sensitivity tv camera without a microscope," FEMS Microbiol Lett. 65(3): 287-290 (1991).

Masuko et al., "Rapid detection and counting of single bacteria in a wide field using a photon-counting tv camera," FEMS Microbiol Lett. 67(2): 231-238 (1991).

Mignon-Godefroy et al., "Solid phase cytometry for detection of rare events," Cytometry. 27(4): 336-44 (1997).

Miraglia et al., "Homogeneous cell- and bead-based assays for high throughput screening using fluorometric microvolume assay technology," J Biomol Screen. 4(4): 193-204 (1999).

Moore et al, "Lymphocyte fractionation using immunomagnetic colloid and a dipole magnet flow cell sorter," J Biochem Biophys Methods. 37(1-2): 11-33 (1998).

Nargessi et al., "Immunoassays for serum c-reactive protein employing fluorophore-labelled reactants," J Immunol Methods. 71(1): 17-24 (1984).

Nargessi et al., "Magnetizable solid-phase fluoroimmunoassay of thyroxine by a sequential addition technique," Clin Chem. 26(12): 1701-3 (1980).

Nebe-von-Caron et al., "Analysis of bacterial function by multicolour fluorescence flow cytometry and single cell sorting," J Microbiol Methods. 42(1):97-114 (2000).

Nelis et al.,"Enzymatic detection of coliforms and *Escherichia coli* within 4 hours," Water Air Soil Pollut. 123:43-52 (2000).

Patterson, "A wide angle camera for photographic search of the ocean bottom," SPIE. C-XII-1-8 (1966).

Perkin Elmer, Inc., GeneScreenTM Hybridization Transfer Membranes: transfer and detection protocols, Application Notes, available at <http://las.perkinelmer.com/>, retrieved Feb. 27, 2007 (11 pages).

Rousseau et al., "New miniaturized highly sensitive immunoassay device for quantitative measurement of soluble or particular antigen or antibodies in a liquid sample," Clin Chem. 45(9): 1685-7 (1999).

Sage et al., "A rapid and nondestructive method for microbiological testing in pharmaceutical manufacturing," Am Biotechnol Lab. (5 pages) (2006).

Schultz et al., "Single-target molecule detection with nonbleaching multicolor optical immunolabels," Proc Natl Acad Sci U.S.A. 97(3):996-1001 (2000).

Susa et al., "Legionella pneumophila infection in intratracheally inoculated T cell-depleted or -nondepleted A/J mice," J Immunol. 160(1):316-21 (1998).

Thomas et al, "Making gold nanoparticles glow: enhanced emission from a surface-bound fluoroprobe," J Am Chem Soc. 122(11): 2655-6 (2000).

Tibbe et al., "Optical tracking and detection of immunomagnetically selected and aligned cells," Nat Biotechnol. 17(12):1210-3 (1999).

Topac, "Colony Counter," <http://www.topac.com/acolyte.html>, retrieved Apr. 12, 2005 (3 pages).

Van Poucke et al. "Solid phase cytometry-based enzymatic detection of coliforms in drinking water within 4 h," Water Supply. 17(2):67-72 (1999).

Van Poucke et al. "Rapid detection of fluorescent and chemiluminescent total coliforms and *Escherichia coli* on membrane filters," J Microbiol Methods. 42(3):233-244 (2000).

Van Poucke et al., "A 210-min solid phase cytometry test for the enumeration of *Escherichia coli* in drinking water," J Appl Microbiol. 89(3):390-6 (2000).

Vidon et al., "A simple chemiluminescence-based method for rapid enumeration of *Listeria* spp. microcolonies," J Appl Microbiol. 90(6):988-93 (2001).

Viinikka et al., "A two-site immunofluorometric assay for human placental lactogen," Clin Chim Acta. 114(1):1-9 (1981).

Waggoner, "Fluorescent Probes for Cytometry," Flow Cytometry and Sorting, Wiley-Liss, 209-225 (1990).

Wellman et al., "Magnetically-assisted transport evanescent field fluoroimmunoassay," Anal Chem. 78(13): 4450-6 (2006).

Wilson, "Use of the IUL Countermat Automatic Colony Counter for Spiral Plated Total Viable Counts," Appl Environ Microbiol. 61(8):3158-3160 (1995).

Wolniak, "BSCI 427 Principles of Microscopy Fall 2004 Syllabus," <http://www.life.umd.edu/cbmg/faculty/wolniak /wolniakmicro. html>, retrieved Nov. 8, 2007 (8 pages).

Yasui et al., "Imaging of Lactobacillus brevis single cells and microcolonies without a microscope by an ultrasensitive chemiluminescent enzyme immunoassay with a photon-counting television camera," Appl Environ Microbiol. 63(11): 4528-33 (1997).

Zhao et al., "Competitive immunoassay for microliter protein samples with magnetic beads and near-infrared fluorescence detection," Anal Chem. 76(7): 1871-6 (2004).

Extended European Search Report for European Application No. 13777731.4, dated Nov. 6, 2015 (5 pages).

Figure 1
A
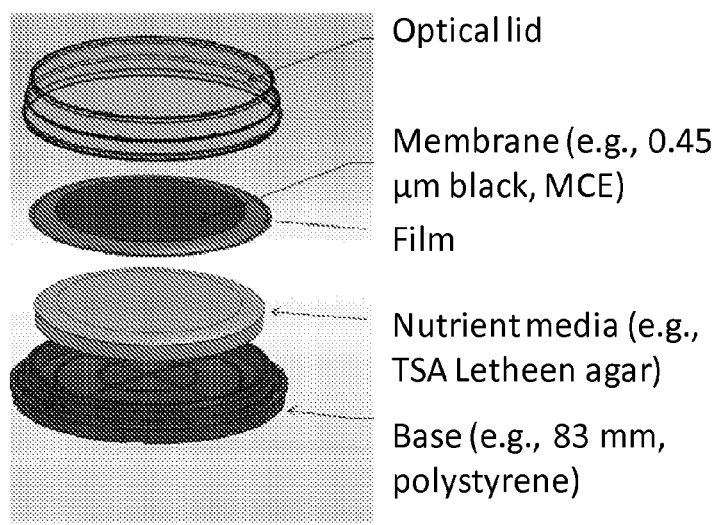
Optical lid
Membrane (e.g., 0.45 µm black, MCE)
Film
Nutrient media (e.g., TSA Letheen agar)
Base (e.g., 83 mm, polystyrene)
B
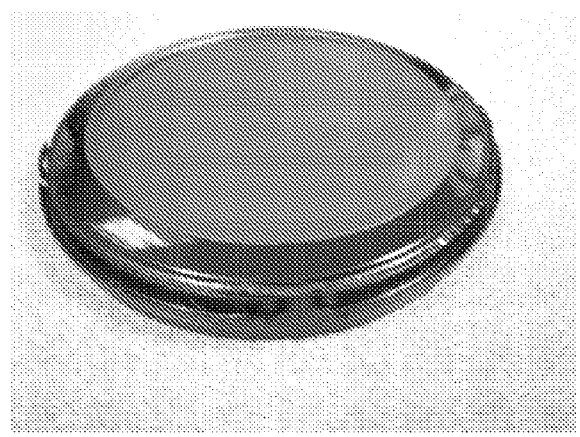

Details of membrane attachment and corralling the organisms

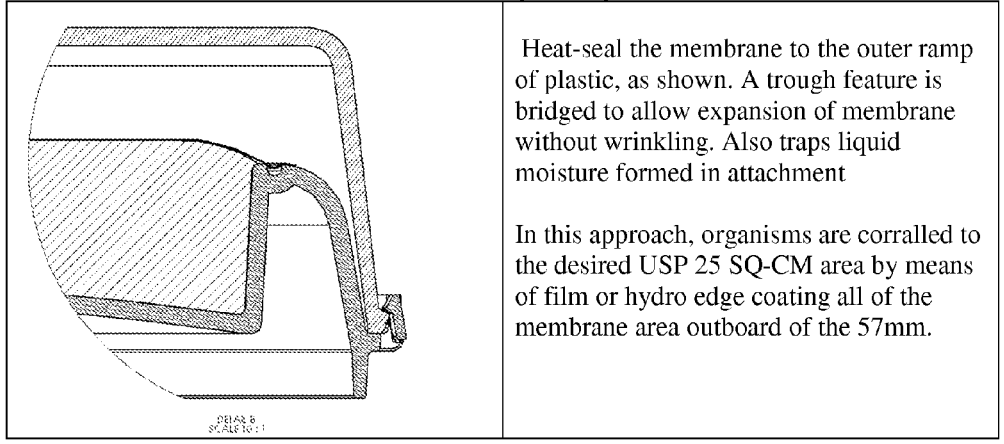

Heat-seal the membrane to the outer ramp of plastic, as shown. A trough feature is bridged to allow expansion of membrane without wrinkling. Also traps liquid moisture formed in attachment In this approach, organisms are corralled to the desired USP 25 SQ-CM area by means of film or hydro edge coating all of the membrane area outboard of the 57mm.

B

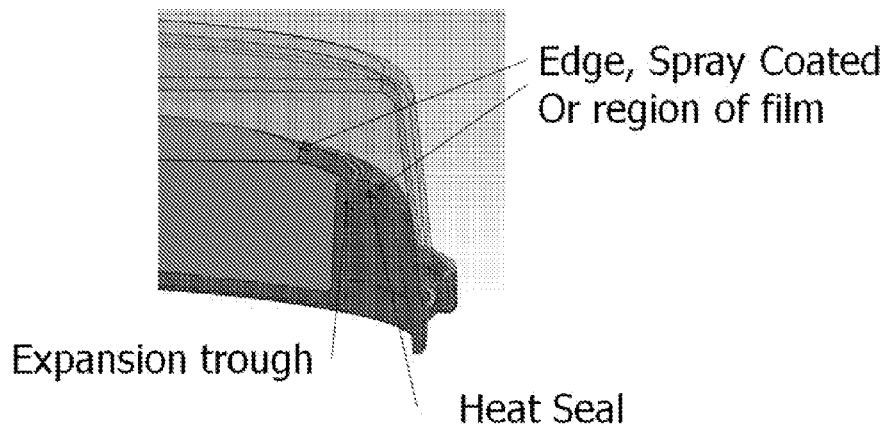

Figure 5
A
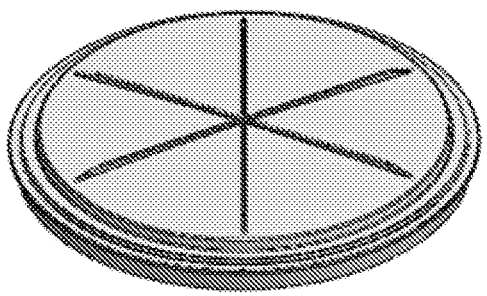
Protective Lid
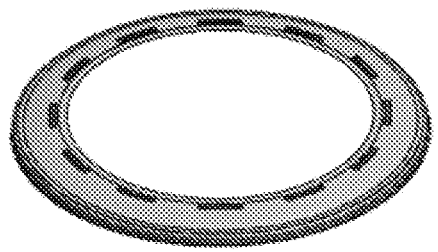
Film (Mask) w/ Fidicual Marks
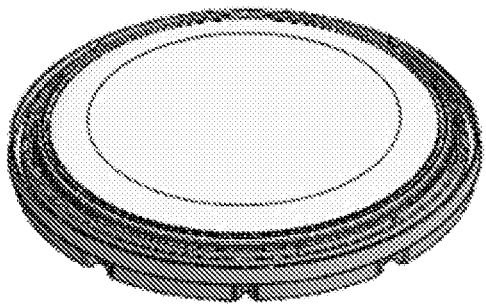
Cassette Base
ID Label

B

Figure 12
A
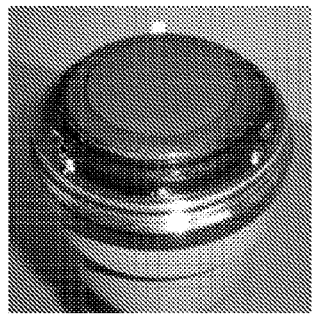
B
 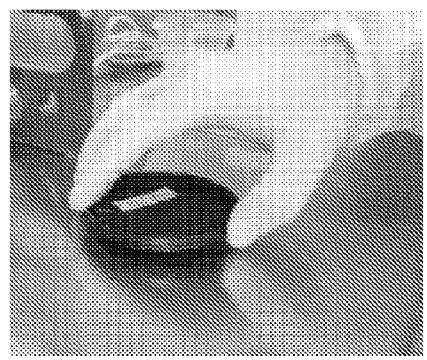
C
 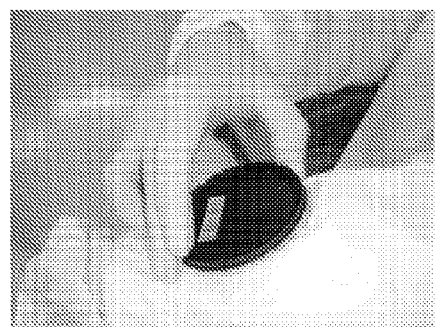

A

B

Figure 14
A
B
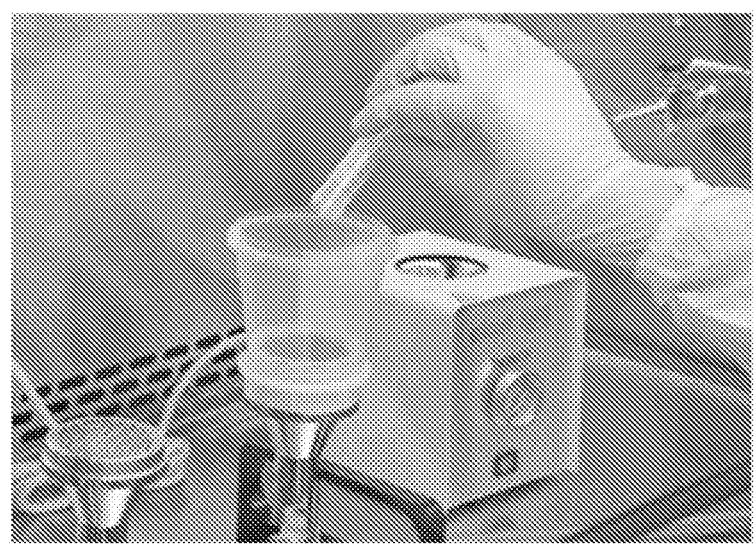

Figure 14
C
D

CELL CULTURING DEVICE

CROSS-REFERENCE TO RELATED APPLICATIONS

This application claims benefit to U.S. Provisional Application No. 61/624,643, filed Apr. 16, 2012, which is hereby incorporated by reference.

BACKGROUND OF THE INVENTION

The invention relates to the fields of cell culture and detection.

In many industries, particularly the food, beverage, healthcare, electronic, and pharmaceutical industries, it is essential to analyze samples rapidly for the degree of contamination by microorganisms, such as bacteria, yeasts, or molds.

One microbial culture technique, called microbial enumeration or colony counting, quantifies the number of microbial cells in a sample. The microbial enumeration method, which is based on in situ microbial replication, generally yields one visually detectable "colony" for each microbial cell in the sample. Thus, counting the visible colonies allows microbiologists to accurately determine the number of microbial cells in a sample. To perform microbial enumeration, bacterial cells can be dispersed on the surface of nutrient agar in Petri dishes ("agar plates") and incubated under conditions that permit in situ bacterial replication. Microbial enumeration is simple, ultra-sensitive, inexpensive, and quantitative but may also be slow.

There is a need for additional culturing devices and methods for rapid microbial enumeration.

SUMMARY OF THE INVENTION

The invention provides devices and kits for capturing and culturing microorganisms, e.g., present in environmental samples. In one aspect, the invention provides a cell culturing device including a base that contains nutrient media for microorganisms; a porous membrane overlaying the nutrient media; and a lid that mates with the base to cover the membrane and the nutrient media. The nutrient media has a flat growth area raised above the base and a circumferential area that slopes from the edge of the flat growth area to the base, and the nutrient media is capable of sustaining growth of microorganisms in the growth area. In certain embodiments, the base includes polystyrene. The base may also include a circumferential groove across which the membrane is sealed. The membrane includes, for example, a mixed cellulose ester membrane. The membrane may be substantially non-radiative and substantially non-reflective and/or black.

In other embodiments, the growth area has a flatness of 100 to 450 μm before collection of a sample or 300 to 500 μm after collection of a sample. The nutrient media may or may not sustain growth of microorganisms in the circumferential area. The membrane may be attached to the base by a film that is sealed to the base. Alternatively, the device may further include a film applied to the base and circumferential area, in which the film adheres the membrane to the base.

In another aspect the invention provides a cell culturing device including, a base that contains nutrient media for microorganisms, in which the nutrient media has a flat growth area (e.g., a flatness of about 100 to 450 microns) raised above the base, in which the nutrient media is capable of sustaining growth of microorganisms in the growth area, a film overlaying the nutrient media, in which the film and the nutrient media have a circumferential area that slopes from the edge of the flat growth area to the base, and the film has an opening to expose a portion of the flat growth area, and a lid that mates to the base to cover the nutrient media. In another embodiment, the device also includes a porous membrane in contact with the exposed growth area.

In another aspect, the invention provides a kit for cell culturing including a cell culturing device that includes, a base that contains nutrient media for microorganisms, in which the nutrient media has a flat growth area (e.g., flatness of about 100 to 450 microns) raised above the base, in which the nutrient media is capable of sustaining growth of microorganisms in the growth area, and a film (e.g., a non-porous film) overlaying the nutrient media, in which the film and the nutrient media have a circumferential area that slopes from the edge of the flat growth area to the base, and the film has an opening to expose a portion of the flat growth area, a porous membrane configured for placement on the exposed portion of the flat growth area; and a lid that mates with the base to cover the membrane and the nutrient media. In another embodiment, the film has fiducial marks for placement of a membrane on the growth area. In one embodiment, the kit also includes a filtration device, such as the device in WO 2007/038478, which is hereby incorporated by reference.

In one embodiment of any of the devices or kits of the invention, the lid may include an optically clear material disposed to allow imaging of the growth area. The lid when attached to the base may also prevent contamination by ingress of microorganisms, in which the lid is separated from the membrane by an air gap. The device may include a unique ID label on the base. The ID label may be a bar code or 2D barcode. The ID label may be used to track the device identity, device compatibility with automated detection instruments and protocols, device expiration date, sterilization history, and other information of interest. The device may also include indentations or protrusions to allow for alignment and gripping by human users or instrumentation, e.g., in the lid and/or the device. In certain embodiments, a device is not compressible in the lateral direction, e.g., to maintain flatness of the growth area. In such embodiment, one or more mechanically supporting elements may be incorporated into the device to provide rigidity in the lateral direction. In other embodiments, the device includes a fiducial mark, e.g., of radiative plastic, printed fluorescent material, embossed fluorescent material, or a through hole exposing fluorescent media, material, or plastics, located, e.g., outside the growth area. For devices with a separable membrane, the fiducial mark may be a through hole in the membrane that is located outside of the area through which a sample is filtered. Such a through hole may expose fluorescent nutrient media, plastic, or printed material. Fiducial marks may be employed to align a membrane with a growth area and/or in the automated alignment of multiple images taken from a device.

In another embodiment, the base mates to the lid to prevent a rotation of greater than about 50 μm of the base relative to the lid.

In another embodiment, the invention provides a device or a kit in which the base has a bottom surface and a side wall extending around the perimeter of and upward from the bottom surface, in which the nutrient media is within the side wall of the base, and the lid has a top surface and a side wall extending around the perimeter of and downward from the top surface; in which the lid reversibly secures to the base (e.g., the lid secures to the base by axial compression or the lid secures to the base by rotation of the lid relative to the base).

In another embodiment, the lid or the base also includes a circumferential rim (e.g., continuous or discontinuous) extending laterally from the side wall of the base or from the side wall of the lid and a first detent extending laterally from the side wall of the base or from the side wall of the lid, in which the circumferential rim has a proximal side facing away from the top of the lid or the bottom of the base, a distal side facing toward the top of the lid or the bottom of the base, and a lateral edge connecting the proximal and distal sides, in which the lid has the circumferential rim and the base has at least one first detent, or the lid has at least one first detent and the base has the circumferential rim, and in which the lid is secured to the base by interengagement between the circumferential rim and the at least one first detent. In another embodiment, at least one first detent extending laterally defines a gap between the first detent and the bottom surface of the base or the top surface of the lid, in which the gap is sized to accept the circumferential rim, and the first detent engages the distal side of the circumferential rim. The first detent may alternatively engage the lateral side of the circumferential rim. The device may include at least one second detent extending laterally from the side wall, in which the circumferential rim includes a kerf, and the second detent engages the kerf. Another embodiment of the invention may include a device in which the distal side of the rim is sloped, and the at least one first detent engages the distal side of the rim by relative rotation of the lid to the base. The device may include a plurality of circumferential rims and first detents, in which the lid secures to the base by relative rotation of 90 degrees or less, e.g., 45 degrees or less. The device may include a stop on the lid or base that arrests rotation of the circumferential rim after a specified amount of rotation.

In another aspect, the invention provides a kit including a cell culturing device containing a base that contains nutrient media for microorganisms; and a porous membrane overlaying the nutrient media, in which the nutrient media has a flat growth area raised above the base and a circumferential area that slopes from the edge of the flat growth area to the base, and in which the nutrient media is capable of sustaining microorganisms in the growth area; a protective lid attached to the base and preventing contamination by ingress of microorganisms, in which the protective lid is separated from the membrane by an air gap; and an optical lid attachable to the base when the protective lid is removed and including an optically clear material disposed to allow imaging of the growth area when attached to the base.

In a further aspect, the invention provides a kit including a cell culturing device containing a base that contains nutrient media for microorganisms, in which the nutrient media has a flat growth area raised above the base, in which the nutrient media is capable of sustaining growth of microorganisms in the growth area, a film overlaying the nutrient media, in which the film and the nutrient media have a circumferential area that slopes from the edge of the flat growth area to the base, and the film has an opening to expose a portion of the flat growth area, a porous membrane configured for placement on the exposed portion of the flat growth area; a protective lid attached to the base and preventing contamination by ingress of microorganisms, in which the protective lid is separated from the growth area by an air gap; and an optical lid attachable to the base when the protective lid is removed and including an optically clear material disposed to allow imaging of the growth area when attached to the base. The kit may also include a filtration device as described herein.

The invention also features a method for monitoring the presence of microorganisms by providing a device or kit of the invention; contacting the growth area of the device with a volume of air or a surface; incubating the device to allow growth of microorganisms; and determining the extent of growth of microorganisms. Exemplary surfaces include industrial and laboratory surfaces and garments. In certain embodiments, the sample is collected by rolling the device so that the circumferential area and growth area contact the surface or passing the volume of air over the growth area. The extent of growth may be determined by optically imaging the growth area. An image may be analyzed to quantify the number of microorganisms. The incubation and determining steps may be repeated to determine colonies of microorganisms that grow over time.

In another aspect, the invention provides a method for monitoring the presence of microorganisms in a sample by providing a device or kit of the invention, filtering a sample through the membrane, placing the membrane on the growth area, incubating the device to allow growth of microorganisms; and determining the extent of growth of microorganisms. The extent of growth may be determined by optically imaging the growth area. An image may be analyzed to quantify the number of microorganisms. The incubation and determining steps may be repeated to determine colonies of microorganisms that grow over time.

By a "substantially non-radiative" object is meant an object that does not emit light, e.g., by fluorescence, phosphorescence, or luminescence.

By a "substantially non-reflective" object is meant an object that reflects less than 25%, 10%, 5%, 1%, or 0.1% of the light used to image the object.

By a "securing member" is meant a component or feature of aspect of a mechanical mechanism that joins or affixes two entities. Exemplary securing members are threads, catches, detents, rims, latches, hooks, clasps, snaps, bayonet mounts, J-shaped hooks, L-shaped hooks, dents, protrusions, ribs, spring tongues, tabs, grooves, stops, notches, holes, kerfs, compression fits, interference fits, jam fits, cams, and cam stops. By "secures" is meant to mate, join or form a union between two entities in which the rotation of the two entities relative to each other is limited.

By "circumferential" is meant around the perimeter. Circumferential is not limited to circular shapes, for the purpose of this invention.

Other features and advantages will be apparent from the following description, the drawings, and the claims.

BRIEF DESCRIPTION OF THE DRAWINGS

FIG. 1A is an exploded view of a device of the invention.
FIG. 1B is a photograph of a device with the cover removed.

FIG. 2A is a cross-sectional view of a device with a protective lid installed before use of the device. FIG. 2B is a cross-sectional view of a device with an optical lid installed.

FIGS. 3A-3B are cross-sectional views showing details of attachment of a membrane to a base. FIG. 3A is a cross-sectional view of a part of a device showing an expansion trough. FIG. 3B is a schematic depiction of a part of a device showing the location of a film or edge coating and expansion trough.

FIGS. 12A-12C are a set of images showing the use of a device in monitoring different types of environmental samples: air (FIG. 12A), surfaces such as work areas (FIG. 12B), and garments such as gloves or sleeves (FIG. 12C).

FIGS. 14A-14D are a set of images showing the monitoring of a liquid sample using a filtration device and a device of the invention. FIG. 14A is a photograph of the assembled filtration device, a protective lid, and a device of the invention. FIG. 14B is a photograph of filtering a sample through the membrane within the filtration device. FIG. 14C is a photograph of the disassembled filtration device, showing the funnel, membrane on the filtration base, protective lid, and a device of the invention. FIG. 14D is a photograph showing the transfer of the membrane to a device of the invention, in which the membrane is placed with the fiducial marks on the circumferential rim and fiducial marks (circumferential through holes) in the membrane allow for alignment of multiple images take of the membrane.

DETAILED DESCRIPTION OF THE INVENTION

The invention features devices and kits for capturing and culturing microorganisms (e.g., bacteria, fungi, or protists) and methods of using the devices and kits to detect microorganisms in environmental samples. The device is useful for rapid environmental monitoring and can be used to collect microorganisms, for example, by rolling the device on a surface. The device is then incubated to allow any microorganisms collected to grow into colonies, which are indicative of microbial contamination.

Device

The cell culturing devices of the invention facilitate the sample collection, sample growth, and detection of microorganisms within a sample. Devices of this invention allow for efficient, cost effective, and robust microorganism monitoring for a wide variety of applications.

The device, e.g., as shown in (FIGS. 1A-1B), includes a base that contains nutrient media overlaid by a porous membrane. The membrane is in conformal contact with the nutrient media. The membrane and nutrient media form a flat growth area surrounded by a sloping circumferential area. In preferred embodiments, the membrane allows nutrients to pass through and sustain microbial growth in the growth area but not in the circumferential area. In one aspect of the invention, the device is useful for automated detection of microorganisms, e.g., using the Growth Direct™ system for rapid colony counting, e.g., as described in U.S. Publication No. 2003/0082516, which is hereby incorporated by reference. The device may be of any appropriate size, e.g., that of a RODAC™ plate.

Figure 2:
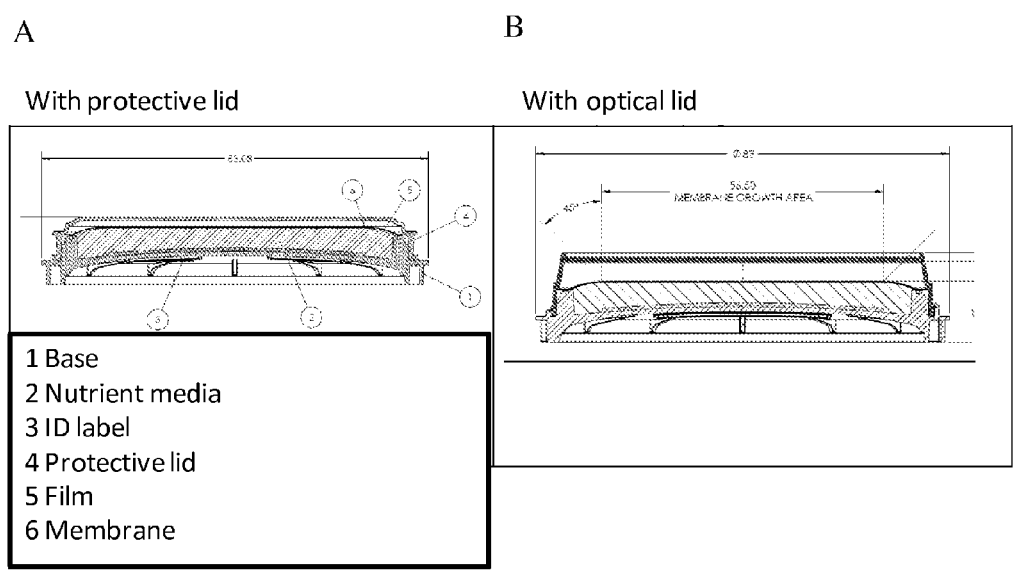
FIGS. 2A-2B are cross-sectional views of a device of the invention.

The base may be substantially non-radiative and non-reflective and may be made of any suitable material, e.g., polystyrene or other plastic. The base may also have a circumferential groove (also referred to as an expansion trough) that can be used for attachment of a membrane (e.g., as shown in FIGS. 2 and 3). The base may be produced by methods known in the art, e.g., injection molding.

Figure 4:
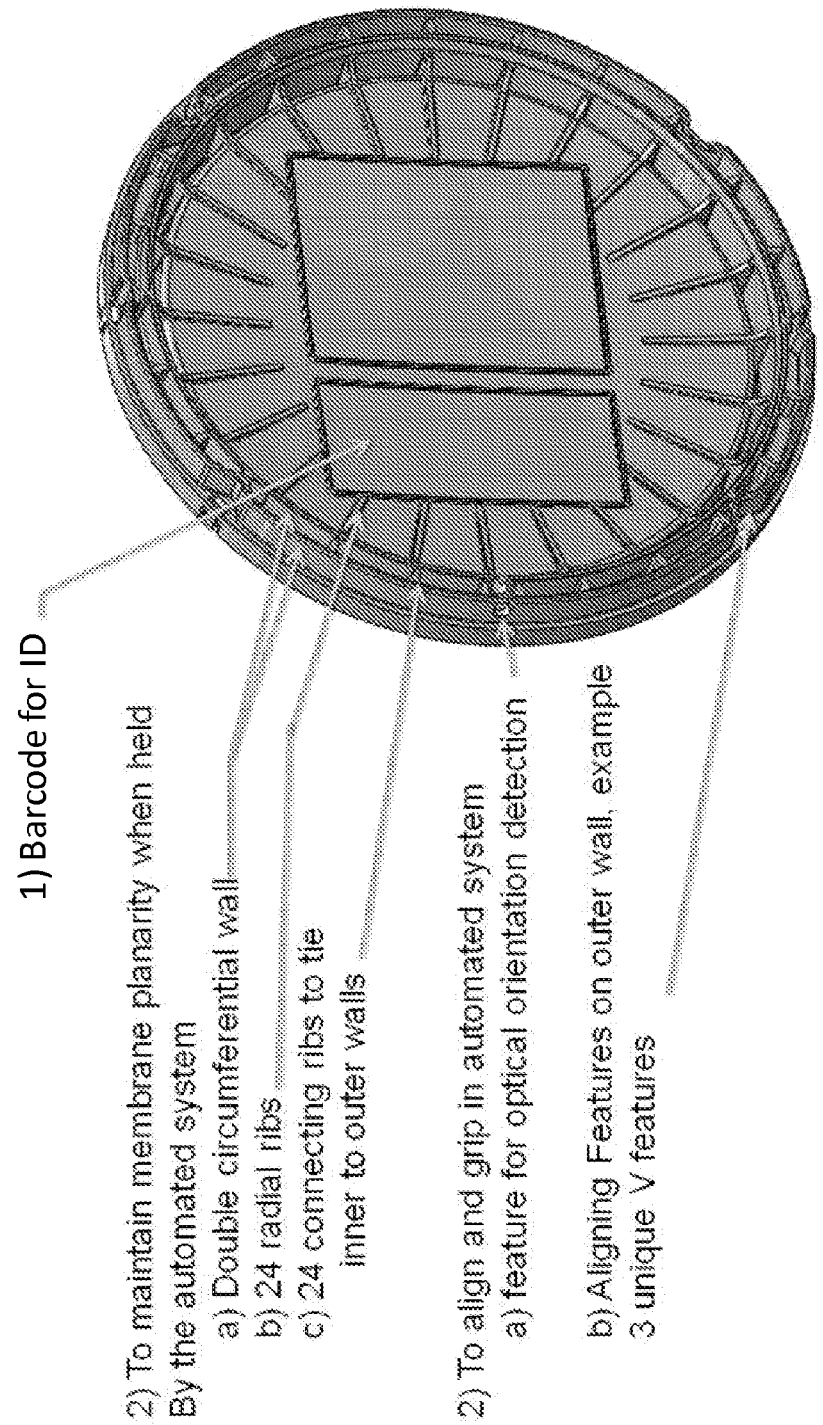
FIG. 4 is a depiction of a base of a device of the invention including a region for application of a bar code, mechanically supporting elements (ribs), a double circumferential side wall, indentations (V features) for alignment and gripping, and a feature for optical alignment.

The device, e.g., the base and/or the lid, may include indentations (e.g., as shown in FIG. 4) or protrusions for gripping or alignment on the device. In certain embodiments, the device is not compressible in the lateral direction. For example, the device may include one or more mechanically supporting elements (FIG. 4) to maintain the flatness of the growth area during handling.

The device includes a porous membrane, e.g., one having fluorescence properties commensurate with detection of autofluorescent microbial microcolonies. For example, the membrane is substantially non-radiative and non-reflective for detection of autofluorescent microbial microcolonies. Membranes may be manufactured from materials including cellulose, cellulose acetate, polystyrene, polyethylene, polycarbonate, polyethylene terephthalate (PET), polyolefin, ethylene vinyl acetate, polypropylene, polysulfone, polytetrafluoroethylene, nylon, and silicone copolymer. The choice of membrane depends, in part, on the type of cell to be cultured (e.g., microorganisms that grow attached to a surface (anchorage-dependent), microorganisms that grow in suspension (anchorage-independent), or microorganisms that grow as attached to a surface or in suspension), degree of permeability, and rate of transfer of fluids and gases. An exemplary membrane is a black mixed cellulose ester membrane (Sartorius AG).

The membrane is placed over the nutrient media so that the membrane and media are in conformal contact. The membrane and nutrient media form a flat growth area raised above the base with a circumferential sloping area around the edges. Such a design makes the device suitable for contact testing, e.g., by rolling the device on a surface. The membrane and nutrient media form a growth area that is flat across an area, e.g., of 10, 15, 20, 25, 30, 35, or 50 cm$^2$, preferably at least at least 25 cm$^2$. The membrane on the nutrient media has a flatness of about 100 to 600 µm, e.g., 200 to 350 µm, e.g., about 300 µm, as fabricated or 300 to 500 µm, e.g., about 450 µm, after collection of sample. The membrane is preferably factory installed and stays wet for the life of the product. The membrane has pores so that microorganisms deposited on the membrane may obtain nutrients from the underlying nutrient media. Examples of membrane pore sizes are 0.45 µm and 0.22 µm.

Solid or semi-solid nutrient growth media can be employed in the present device. Examples include Sabouraud dextrose agar (SDA), R2A agar, tryptic soy agar (TSA) letheen, and plate count agar (PCA). The media may be poured onto the base in a molten liquid state and then allowed to solidify into a flat growth area that is raised above the base and a circumferential area that slopes from the edge of the flat growth area to the base. The flatness of the growth area may be controlled by surface tension and by filling normal to gravity. The flatness of the growth area may also be achieved using several alternate methods. For example, one method to achieve a flat growth area includes pouring molten nutrient media onto the underside of a pre-attached, wet membrane. In this alternate method, the membrane is pre-attached to a base that has an opening on the bottom. The opening is used to fill molten nutrient media, e.g., agar. This opening is then sealed post filling by a cover or film. The membrane is circumferentially sealed to prevent leakage. The membrane expands or inflates during the filling process and may be shaped by trapping within a nest or cavity of appropriate shape. Another method to achieve flatness is to pre-bow the base mid section downward by approximately 150 to 200 µm, e.g., using vacuum. The nutrient media is poured, and, once the media solidifies with a concave surface, the bowing force is released and the growth area springs back to the flat state. Alternatively, the nutrient media may be a liquid media held in a porous matrix, which is shaped to have a flat growth area and sloping circumferential area.

The membrane is preferably secured to prevent peeling during use. The membrane may be installed by heat sealing to the base, e.g., by bridging over a circumferential groove. The groove (FIG. 3A) allows expansion of the membrane without wrinkling. The groove also traps any moisture formed during the attachment. Alternatively, the membrane may be attached to the device using a circumferential film, e.g., of PET, co-PET, acetate, or polyimide, that may be used to define the edges of the growth area. The film may be made black. The film may be substantially non-radiative and/or non-reflective. The film may contain several layers (FIG. 3B). Such layers allow for heat fusion to the membrane without damaging the membrane, low fluorescence, and/or low reflectance. A film may also cover the circumferential area to prevent growth of microorganisms outside the flat growth area. This arrangement is beneficial in confining growth to an area of the device, e.g., for imaging or visual inspection.

In alternative design, a device does not include an integral membrane. This device also includes a nutrient media raised above the base, a flat growth area, a film overlaying the circumferential area of the nutrient media (FIGS. 5A and 5B), and the circumferential area that slopes from the edge of the flat growth area to the base. The device includes a film that overlays the circumferential area (in whole or in part), and the film has an opening to expose a portion of the flat growth area. The opening in the film and the nutrient media form a growth area that is flat across an area, e.g., of 10, 15, 20, 25, 30, 35, or 50 cm$^2$, preferably at least at least 25 cm$^2$. Suitable films include any non-porous or hydrophobic plastic or material, e.g., PET, co-PET, acetate, or polyimide. The film may be made black. The film may be substantially non-radiative and/or non-reflective. The growth area provides a surface where a porous membrane, e.g., exposed, to a sample may be overlaid. The nutrient media provides sustained growth of organisms on the top surface of the overlaid membrane, thereby providing a device for cell culturing and detection of contamination.

The device also includes a lid. The lid is for example a protective lid (FIG. 2A) that does not contact the membrane and prevents contamination of the device prior to use. The lid may also be an optical lid (FIG. 2B) with an optically clear window for imaging the growth area, e.g., with visible or UV light. An exemplary material for the lid is Zeonor® 1060R (polycycloolefin resin; Zeon Chemicals LP). Glass may also be employed. The optical lid may also be used as a protective lid prior to use. The lid mates to the base to seal the membrane and nutrient media from outside contamination. The lid may be produced by methods known in the art, e.g., injection molding. All or part of the lid may be non-radiative and/or non-reflective.

A lid secures to the base using securing members present on both the lid and the base. The lid and base may secure or engage reversibly, in which the lid and base may be separated and reattached multiple times. Securing the lid to the base affixes the lid relative to the base in the axial direction (z-axis), thereby sealing the device. Securing members may provide alignment of the lid relative to the base securing in the lateral directions (x-axis and y-axis). Preferably, the lid protects the base and also prevents rotation of the lid relative to the base, e.g., to less than 50 µm.

Figure 6:
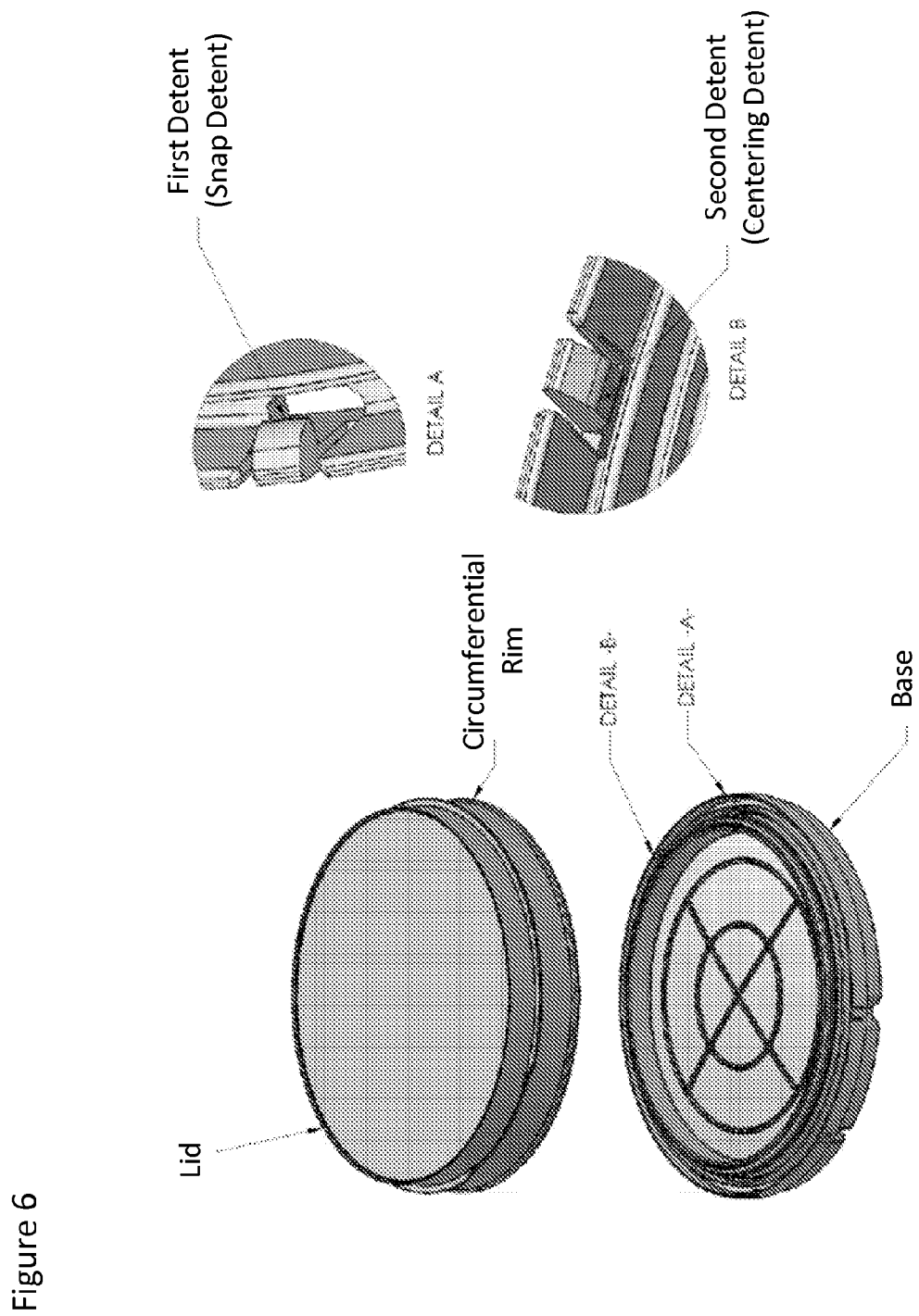
FIG. 6 is a schematic depiction of a device of the invention including an optical lid with a circumferential rim and a base with three first detents (Snap detent, Detail A of FIG. 6) and three second detents (Centering detents, Detail B of FIG. 6).

A lid may be secured to the base with axial compression. For example, a circumferential rim (FIG. 6) on the lid and detents (snap detents, FIG. 6, Detail A) on the base may be used to secure the lid to the base once an axial force is applied to the lid. The detent is deflected as the circumferential rim passes the detent. The circumferential rim rests in a gap between the snap detent and the bottom surface of the base. The snap detent (Detail A of FIG. 6) may have a pointed protrusion to reduce the contacting surface area of the snap detent, thus increasing the force per area applied to the circumferential rim. In addition to the snap detents, centering detents can be used that apply pressure to the lateral edge of a circumferential rim (Detail B of FIG. 6), thus fixing the position of the lid. The reproducibility of the optical lid position relative to the base is important for improving the consistency of automated sample imaging. Securing and preventing movement of the optical lid improves the reproducibility of the automated image analysis.

Figure 7:
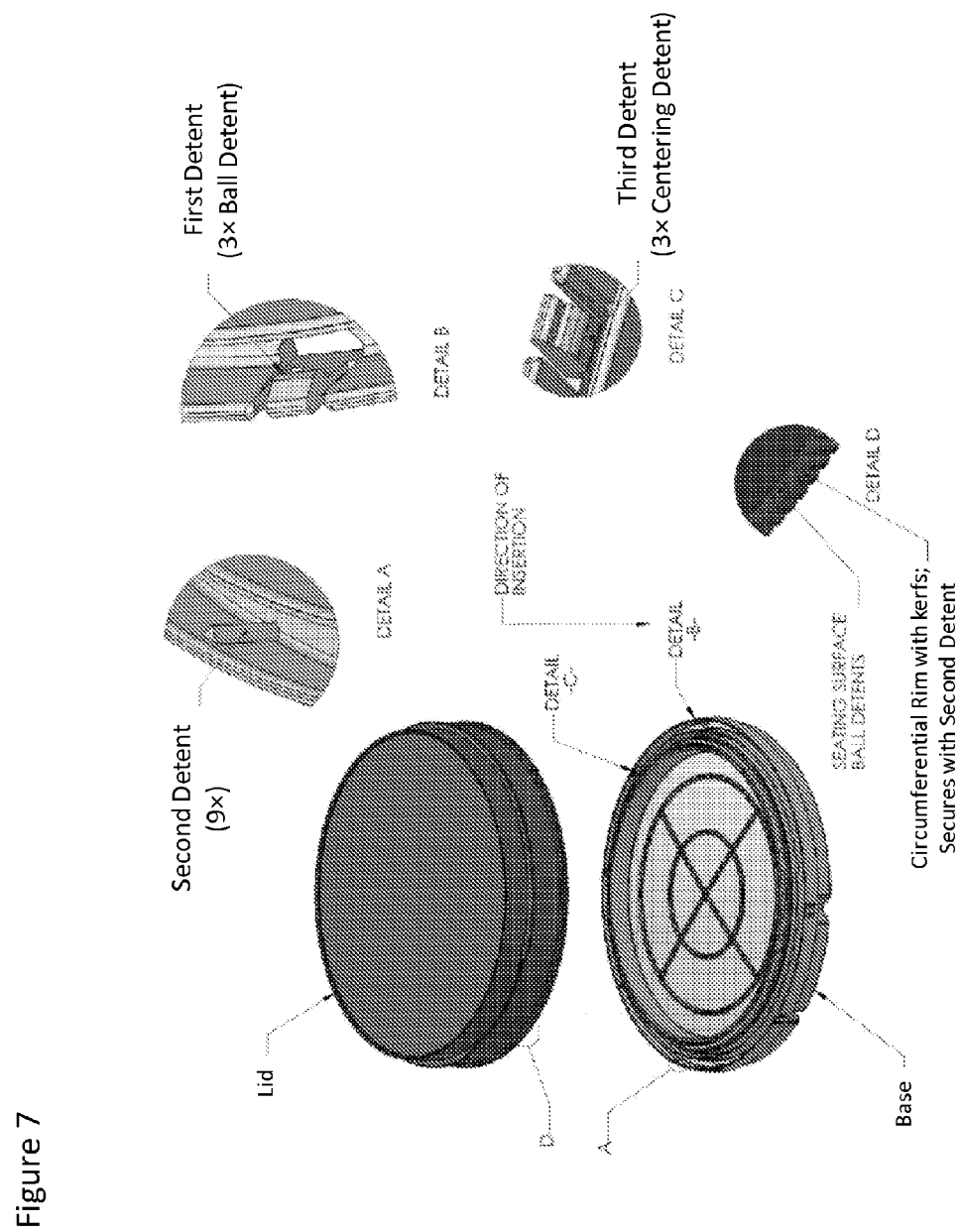
FIG. 7 is a schematic depiction of a device of the invention including a lid with a kerfed circumferential rim (Detail D in FIG. 7) and a base with three first detents (Ball detents, Detail B in FIG. 7), and three third detents (Centering detents, Detail C in FIG. 7), and nine second detents (Detail A in FIG. 7) that are configured to fill within the kerfs.

In an alternative embodiment, the base may include multiple ball detents (Detail B of FIG. 7), multiple second detents (Detail A of FIG. 7), and multiple centering detents, (Detail C of FIG. 7), around perimeter of the base. The lid is secured to the base first detent by a circumferential rim (FIG. 7). The second detents help align the lid relative to the base. The kerfed circumferential rim (Detail D of FIG. 7)

prevents rotation of the lid relative to the base because the second detents (Detail A of FIG. 7) fill the kerfs of the rim.

Figure 8:
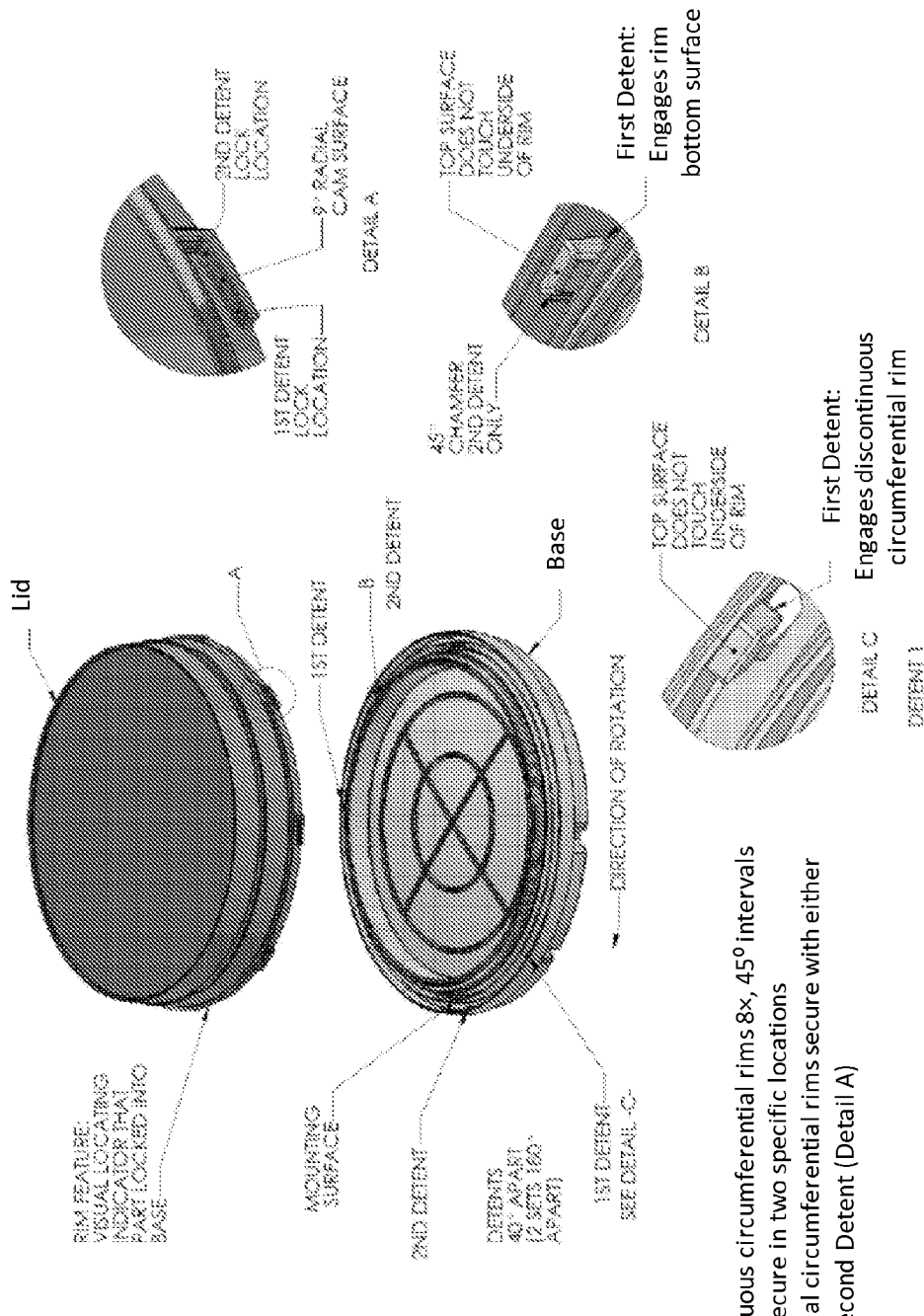
FIG. 8 is a schematic depiction of a device of the invention including a lid having a discontinuous circumferential rim (see Detail A in FIG. 8) and a base with two types of detents that are complementary to the discontinuous rim of the lid. The detents of the base are separated by about 40 degrees relative to the circumference. The first detents (see Detail C of FIG. 8) and second detents (see Detail B of FIG. 8) engage the discontinuous rim. The lid also has a visual indicator (rim feature).

A lid may be secured to the base with a rotational motion of less than or equal to 90 degrees. For example, the lid may be have a series of discontinuous circumferential rims (FIG. 8, Detail A). The discontinuous circumferential rims may or may not be evenly distributed around the perimeter, each about 40 degrees apart (FIG. 8). A series of detents may be located on the base (FIG. 8). Two variations of detents are shown (Detail C and Detail B of FIG. 8), but a single type may be employed. The first detent engages to the top edge (distal edge adjacent to top surface of the lid) of the circumferential rim in the portion opposite the vertical portion of the discontinuous circumferential rim. The second detent engages to the top edge (distal edge adjacent to top surface of the lid) of the circumferential rim.

Figure 9:
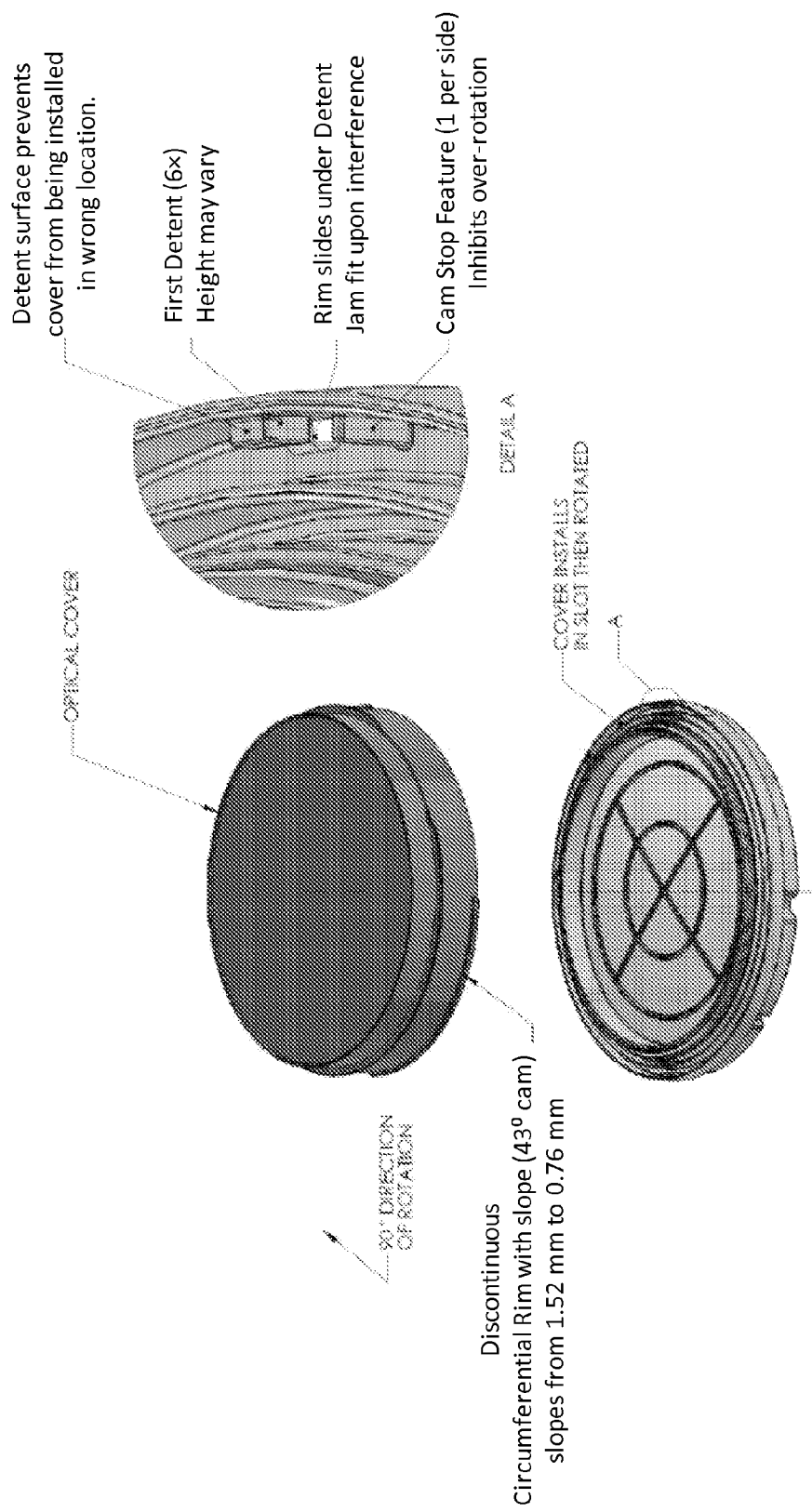
FIG. 9 is a schematic depiction of a device of the invention including a lid that has two discontinuous, sloping circumferential rims and a base with three first detents and two stops (Cam Stop, Detail A in FIG. 9).

A lid may also be secured to the base with a rotational motion of less than or equal to 90 degrees. For example, the base includes multiple detents (Detail A of FIG. 9) sized and shaped to reversibly secure to a discontinuous, sloped circumferential rim (FIG. 9). The first detent has a horizontal length with a top surface that prevents lid from being installed in wrong location. The first detent facilitates a jam fit by providing an upper boundary that increasingly interacts with the variable height (sloped) discontinuous circumferential as the lid is twisted relative to the base. A stop (cam stop, Detail A of FIG. 9) provides a rotational boundary for the discontinuous circumferential rim. The increasing height of the circumferential rim engages the first detent as the rim is turned about 90 degrees, thereby inducing a jam fit. The cam stop prevents over-rotation, providing a stop for the leading edge of the circumferential rim.

Additional non-limiting exemplary securing members and mechanisms for securing a lid to the base include: threads, clamps, gaskets, magnets, crown caps, and friction fits. For example, a lid of the device of the invention may be configured with a series of threads. A base of the invention may be configured with a complimentary series of threads, for securing the lid to the base.

The protective lid and the optical lid may attach to the same base using the same or different mechanisms. The securing members may be on the lid or the base. For example, the circumferential rim may be on the lid, and the detents on the base. Alternatively, the detents may be on the lid, and the circumferential rim on the base. Circumferential rim may also be on the outer or inner perimeter of the side wall of the lid or the base.

The device may include features that indicate successful securing of the lid to the base. For example, a rim feature on a lid (FIG. 8) may be above a base and be visible before the lid is secured to the base. Once the lid is secured to the base, the rim feature is not visible above the base, thereby indicating a successful union of the lid and the base. The device may include securing members compatible with automation. For example, a securing member may be sized and shaped such that robotic transfer arms may engage a securing member, thereby facilitating the automated use of the device.

Figure 5:
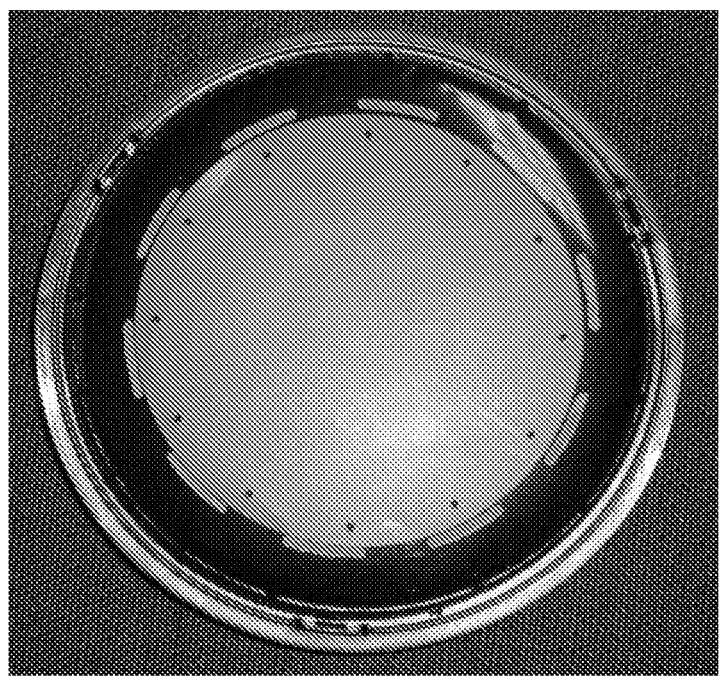
FIG. 5A is an exploded view of a device of the invention including a protective lid, a circumferential film with fiducial marks (dashes), a base with nutrient media and a growth area, and a bar code label.
FIG. 5B is a photograph of a device of the invention including a circumferential film with fiducial marks (dashes), a base with nutrient media and a growth area, and a membrane with circumferential fiducial through holes overlaying the growth area and partially overlaying the circumferential film.
Figure 10:
FIG. 10 is a photograph of a device of the invention including a base, a membrane overlaying a nutrient media, and a circumferential area which slopes to the base. In addition, fiducial marks (dots) can be seen in the circumferential area.

The device may also include a fiducial mark, e.g., printed fluorescent material, embossed fluorescent material, radiative plastic, or a through hole exposing fluorescent media, material, or plastics. Other fiducial marks are known in the art. The fiducial mark may be outside the growth area (FIG. 5B and FIG. 10). The fiducial mark may help align a membrane with the device (FIG. 5B). A fiducial mark may be used to align multiple images acquired from the same device, e.g., taken at different times, or the fiducial mark may be used to align the device within an imager. The fiducial marks may be at any position on the device that is suitable for imaging, e.g., the base, the circumferential area, the growth area, or the lid.

The device may also have a unique ID label imprinted or affixed on the device to aid in automated handling or sample tracking, e.g., by the Growth Direct™ system. The ID label may be a bar code or 2D barcode. The ID label may be used to track the device identity, device compatibility with instruments and protocols, device expiration date, sterilization history, and other information of interest.

Methods of Use

Figure 11:
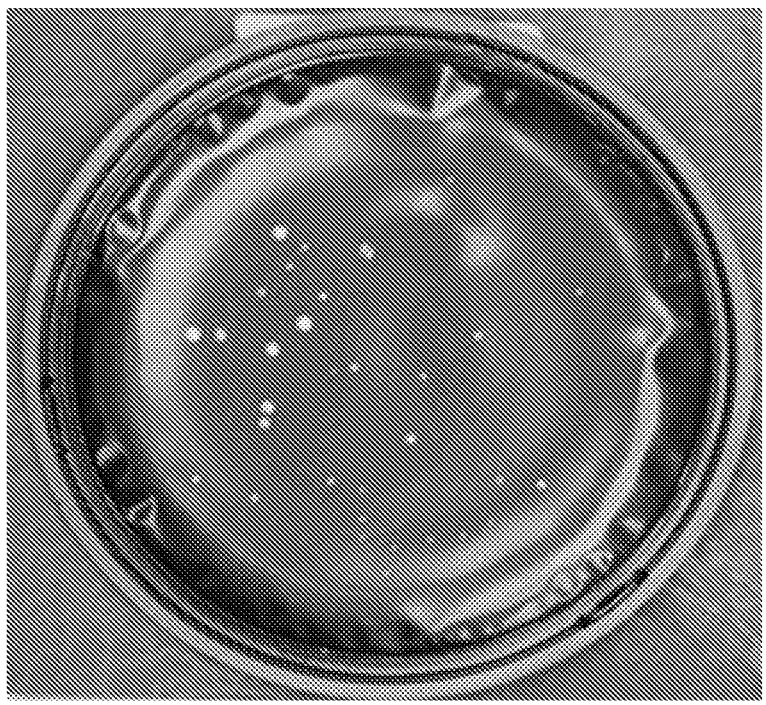
FIG. 11 is a photograph of microbial colonies grown on a device and visible to the human eye.

The devices can be used to monitor the presence of microorganisms, e.g., in the environment. Environmental samples may include, without limitation, air, surfaces, and garments. The devices and kits of the invention may be used in any situation where microbial contamination needs to be rapidly detected, e.g., laboratories, hospitals, manufacturing areas, and "clean rooms" for nanotechnology manufacturing and applications. Exemplary surface samples include surfaces of stainless steel, glass or granite work surfaces, walls, floors and equipment surfaces. Surface may also include anatomical structures such as fingers and foreheads. Exemplary garment samples include jacket sleeves, gloves, chest plate and any other portion of wearable garment. The method may include: contacting the growth area of the device with a volume of air or a surface; incubating the device to allow growth of microorganisms (incubation may occur at, above, or below room temperature); and determining the extent of growth of microorganisms, e.g., by manual counting or by automated counting of colonies (as shown in FIG. 11). Any culturable microorganism, including bacteria, cyanobacteria, protozoa, and fungi may be employed in conjunction with the device described herein. The device can be used for aerobic and anaerobic testing.

The sample may be collected by rolling the device so that the circumferential area and the growth area contact the surface. The surface can be, e.g., work surfaces such as a laboratory surface or industrial surface (FIG. 12B), garments (FIG. 12C), or gloves (FIG. 12C). In another aspect of the invention, air samples can be tested by passing a volume of air over the growth area, e.g., in an air monitor (FIG. 12A) or by leaving the device uncovered for a period of time.

After sample collection, the device is typically covered using the optical cover and is incubated for microorganisms to grow, e.g., in an incubator at temperatures above or below room temperature. In one embodiment, after sample collection, the device is placed within the Growth Direct™ system for incubation and imaging. The device may be imaged at predefined intervals of time, and microorganisms may be detected by suitable methods known in the art, e.g., fluorescence (via autofluorescence or stains), reflectance, or absorbance. Alternatively, vital stains may be introduced into the nutrient media and absorbed into the microorganisms during growth. Detection may be repeated to discern growing colonies from non-growing microorganisms or debris. Images of microorganisms may be recorded, either digitally or with film. The optical lid of the device may be removed manually or using automation and replaced with a protective lid during storage. The protective lid may reversibly secure the base using one or more securing members. An optical lid may reversibly secure the base using one or more securing members.

Alternatively the sample may be collected by filtering a sample through a membrane and then applying the membrane to the device of the invention. For example, a membrane and filtration device (FIGS. 13A and 13B, and FIG.

Figure 13:
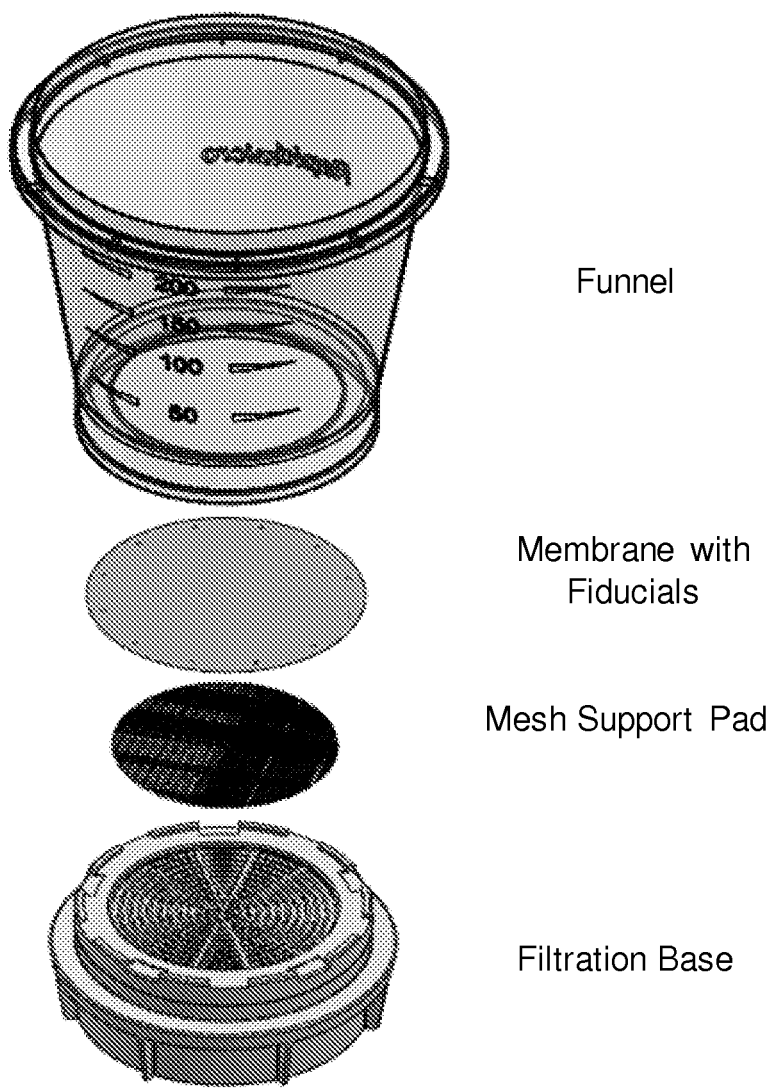
FIG. 13A is an exploded view of a filtration device including a funnel, a membrane with fiducial marks, a mesh support pad, and a filtration base.
FIG. 13B is a photograph of an assembled filtration device.
Figure 13:

14A) may be used to filter a liquid sample, thus collecting any contaminating microorganisms on the membrane. As shown in FIGS. 13A-13B, an exemplary filtration device includes a funnel that traps a membrane to a filtration base. The membrane is supported by a mesh support pad to maintain flatness during filtration. Other filtration devices are known in the art, e.g., as described in WO 2007/038478. A sample of interest is passed through the membrane to collect microorganisms (FIG. 14B). The membrane is removed from the filtration device and overlaid onto the nutrient media of a device configured to accept a membrane (FIGS. 14C-14D). The membrane may be aligned relative to the fiducial marks on the film (dashes). The membrane may include fiducial marks, e.g., through holes in the region outside of the filtered area. Such through holes can be used to expose fluorescent media, plastic, or printed material that is otherwise covered by the membrane. The membrane may be larger diameter than the exposed growth area and overlap the circumferential film. The membrane may adhere to the growth area by wetting from the nutrient. The membrane and device are then covered, incubated, and imaged as described above.

Other methods and instruments for manual or automated colony counting that can be used with the device are known in the art.

Kit for Environmental Monitoring and Filtering

The invention also features a kit which includes the device, a protective lid, and an optical lid. The kit may be shipped with a protective cover installed on the device. The device with the protective cover and the optical cover may be packaged separately or together in sterile packaging. In use, the protective cover is removed, the sampling is done, and the optical cover is then installed.

Alternatively, the invention also features a kit which includes the device, a protective lid, a membrane, and an optical lid. The kit may be shipped with a protective cover installed on the device. The device with the protective cover, membrane and the optical cover may be packaged separately or together in sterile packaging. In use, the protective cover is removed, the sampling is done, and the optical cover is then installed. Such kits may also include a filtration device as discussed herein.

Other Embodiments

All publications, patents, and patent applications mentioned in the above specification are hereby incorporated by reference. Various modifications and variations of the described method and system of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the art are intended to be within the scope of the invention.

Other embodiments are in the claims.

What is claimed is:

1. A cell culturing device comprising:
   (a) a base that contains nutrient media for microorganisms;
   (b) a porous membrane overlaying the nutrient media, wherein the nutrient media has a flat growth area raised above the base and a circumferential area that slopes from the edge of the flat growth area to the base, and wherein the nutrient media is capable of sustaining growth of microorganisms in the growth area; and
   (c) a lid that mates with the base to cover the membrane and the nutrient media.

2. The device of claim 1, wherein the growth area has a flatness of about 100 to 450 microns before collection of a sample or about 300 to 600 microns or less after collection of a sample.

3. The device of claim 1, wherein the membrane is not porous in the circumferential area or the membrane is attached to the base by a film that is sealed to the base.

4. The device of claim 1, further comprising a film applied to the base and circumferential area, wherein the film adheres the membrane to the base.

5. A cell culturing device comprising:
   (a) a base that contains nutrient media for microorganisms, wherein the nutrient media has a flat growth area raised above the base, wherein the nutrient media is capable of sustaining growth of microorganisms in the growth area,
   (b) a film overlaying the nutrient media, wherein the film and the nutrient media have a circumferential area that slopes from the edge of the flat growth area to the base, and the film has an opening to expose a portion of the flat growth area, and
   (c) a lid that mates with the base to cover the nutrient media.

6. The device of claim 5, further comprising a porous membrane releasably in contact with the exposed growth area.

7. A kit for cell culturing comprising:
   (a) a cell culturing device comprising:
      (i) a base that contains nutrient media for microorganisms, wherein the nutrient media has a flat growth area raised above the base, wherein the nutrient media is capable of sustaining growth of microorganisms in the growth area, and
      (ii) a film overlaying the nutrient media, wherein the film and the nutrient media have a circumferential area that slopes from the edge of the flat growth area to the base, and the film has an opening to expose a portion of the flat growth area;
   (b) a porous membrane configured for placement on the exposed portion of the flat growth area; and
   (c) a lid that mates with the base to cover the membrane and the nutrient media.

8. The device of claim 5, wherein the growth area has a flatness of about 100 to 450 microns.

9. The device of claim 5, wherein the film is not porous or the film has fiducial marks for placement of a membrane on the growth area.

10. The device of claim 6, wherein the membrane has through holes that expose fluorescent nutrient media, plastic, or printed material.

11. The device of claim 6, wherein the membrane comprises a mixed cellulose ester membrane.

12. The device of claim 6, wherein the membrane is substantially non-radiative and substantially non-reflective or black.

13. The device of claim 5, wherein the base comprises polystyrene.

14. The device of claim 5, further comprising a fiducial mark.

15. The device of claim 14, wherein the fiducial mark is outside the growth area.

16. The device of claim 15, wherein the fiducial mark comprises radiative plastic, printed fluorescent material, or embossed fluorescent material.

17. The device of claim 5, wherein the lid comprises an optically clear material disposed to allow imaging of the growth area.

18. The device of claim 5, wherein the lid when attached to the base prevents contamination by ingress of microorganisms, and wherein the lid is separated from the membrane by an air gap.

19. The device of claim 5, wherein the base mates to the lid to prevent a rotation of greater than about 50 µm of the base relative to the lid.

20. The device of claim 5, wherein the base has a bottom surface and a side wall extending around the perimeter of and upward from the bottom surface, wherein the nutrient media is within the side wall of the base, and the lid has a top surface and a side wall extending around the perimeter of and downward from the top surface; wherein the lid reversibly secures to the base.

21. The device of claim 20, wherein the lid secures to the base by axial compression or by rotation of the lid relative to the base.

22. The device of claim 20, further comprising a circumferential rim extending laterally from the side wall of the base or from the side wall of the lid and a first detent extending laterally from the side wall of the base or from the side wall of the lid, wherein the circumferential rim has a proximal side facing away from the top of the lid or the bottom of the base, a distal side facing toward the top of the lid or the bottom of the base, and a lateral edge connecting the proximal and distal sides,
wherein the lid has the circumferential rim and the base has at least one first detent, or the lid has at least one first detent and the base has the circumferential rim, and wherein the lid is secured to the base by interengagement between the circumferential rim and the at least one first detent.

23. The device of claim 22, wherein the circumferential rim is continuous around the side wall of the base or the side wall of the lid.

24. The device of claim 22, wherein the at least one first detent extending laterally defines a gap between the first detent and the bottom surface of the base or the top surface of the lid, wherein the gap is sized to accept the circumferential rim, and the first detent engages the distal side of the circumferential rim.

25. The device of claim 22, wherein the at least one first detent engages the lateral side of the circumferential rim.

26. The device of claim 22, further comprising at least one second detent extending laterally from the side wall, wherein the circumferential rim comprises a kerf, and the second detent engages the kerf.

27. The device of claim 22, wherein the circumferential rim is not continuous along the circumference of the side wall of the base or the lid.

28. The device of claim 27, wherein the distal side of the rim is sloped, and the at least one first detent engages the distal side of the rim by relative rotation of the lid to the base.

29. The device of claim 28, further comprising a plurality of circumferential rims and first detents, wherein the lid secures to the base by relative rotation of 90 degrees or less.

30. The device of claim 28, further comprising a stop on the lid or base that arrests rotation of the circumferential rim after a specified amount of rotation.

31. A method for monitoring the presence of microorganisms in the environment, the method comprising the steps of:
(a) providing a device of claim 1;
(b) contacting the growth area of the device with a volume of air or a surface;
(c) incubating the device to allow growth of microorganisms; and
(d) determining the extent of growth of microorganisms.

32. A method for monitoring the presence of microorganisms in a sample, the method comprising the steps of:
(a) providing a device of claim 5 and a porous membrane;
(b) filtering a sample through the membrane;
(c) placing the membrane on the growth area;
(d) incubating the device to allow growth of microorganisms; and
(e) determining the extent of growth of microorganisms.

33. The method of claim 32, wherein step (e) comprises optically imaging the growth area.

34. The method of claim 33, further comprising analyzing the image to quantify the number of microorganisms.

35. The method of claim 33, further comprising repeating steps (d) and (e) to determine growing colonies of microorganisms.

36. A kit comprising:
(a) a cell culturing device comprising:
   i) a base that contains nutrient media for microorganisms, and
   ii) a porous membrane overlaying the nutrient media, wherein the nutrient media has a flat growth area raised above the base and a circumferential area that slopes from the edge of the flat growth area to the base, and wherein the nutrient media is capable of sustaining microorganisms in the growth area;
(b) a protective lid attached to the base and preventing contamination by ingress of microorganisms, wherein the protective lid is separated from the membrane by an air gap; and
(c) an optical lid attachable to the base when the protective lid is removed and comprising an optically clear material disposed to allow imaging of the growth area when attached to the base.

37. A kit for cell culturing comprising:
(a) a cell culturing device comprising:
   i) a base that contains nutrient media for microorganisms, wherein the nutrient media has a flat growth area raised above the base, wherein the nutrient media is capable of sustaining growth of microorganisms in the growth area, and
   ii) a film overlaying the nutrient media, wherein the film and the nutrient media have a circumferential area that slopes from the edge of the flat growth area to the base, and the film has an opening to expose a portion of the flat growth area,
(b) a porous membrane configured for placement on the exposed portion of the flat growth area;
(c) a protective lid attached to the base and preventing contamination by ingress of microorganisms, wherein the protective lid is separated from the growth area by an air gap; and
(d) an optical lid attachable to the base when the protective lid is removed and comprising an optically clear material disposed to allow imaging of the growth area when attached to the base.

38. The device of claim 1, wherein the nutrient media is not capable of sustaining growth of microorganisms in the circumferential area.

39. The kit of claim 36, wherein the nutrient media is not capable of sustaining growth of microorganisms in the circumferential area.

* * * * *

UNITED STATES PATENT AND TRADEMARK OFFICE
CERTIFICATE OF CORRECTION

PATENT NO. : 10,407,707 B2
APPLICATION NO. : 14/394505
DATED : September 10, 2019
INVENTOR(S) : Douglas J. Browne Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 444 days.

Signed and Sealed this
Thirtieth Day of June, 2020

Andrei Iancu
*Director of the United States Patent and Trademark Office*